US 8,287,582 B2

(12) United States Patent
Dorn

(10) Patent No.: US 8,287,582 B2
(45) Date of Patent: Oct. 16, 2012

(54) LOADING AND DELIVERY OF SELF-EXPANDING STENTS

(75) Inventor: Jurgen Dorn, Munich (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1637 days.

(21) Appl. No.: 10/552,886

(22) PCT Filed: Apr. 28, 2004

(86) PCT No.: PCT/EP2004/004486
§ 371 (c)(1),
(2), (4) Date: Nov. 18, 2005

(87) PCT Pub. No.: WO2004/096091
PCT Pub. Date: Nov. 11, 2004

(65) Prior Publication Data
US 2007/0083256 A1    Apr. 12, 2007

(30) Foreign Application Priority Data
Apr. 28, 2003 (GB) .................................. 0309616.1

(51) Int. Cl.
*A61F 2/06* (2006.01)
(52) U.S. Cl. ........................................ 623/1.11
(58) Field of Classification Search .............. 623/1.11, 623/1.12
See application file for complete search history.

(56) References Cited

U.S. PATENT DOCUMENTS
4,576,534 A * 3/1986 Barth et al. ................... 411/412
4,580,568 A * 4/1986 Gianturco ..................... 606/198
(Continued)

FOREIGN PATENT DOCUMENTS
DE         10016920        10/2001
(Continued)

OTHER PUBLICATIONS
USPTO Office Action in U.S. Appl. No. 10/572,191, dated Mar. 25, 2008.

*Primary Examiner* — Gary Jackson
*Assistant Examiner* — Eric Blatt
(74) *Attorney, Agent, or Firm* — Rutan & Tucker LLP

(57) ABSTRACT

A covered self-expanding stent (20) can be restrained against axial movement with a pusher (40) within the lumen of the stent that carries a spiral of wire (48) that provides protrusions that are accommodated within a luminal covering layer (24) radially inside the stent body. The protrusions distribute the stress over the full length of the stent. The pusher can be removed from the stent lumen by "unscrewing" the spiral relative to the covering layer (24). When the stent expands, the pusher can be withdrawn proximally, out of the stent lumen, without any need for rotatory movement.

27 Claims, 2 Drawing Sheets

U.S. PATENT DOCUMENTS

| | | | |
|---|---|---|---|
| 5,458,605 A | 10/1995 | Klemm | |
| 5,569,296 A | 10/1996 | Marin et al. | |
| 5,619,878 A * | 4/1997 | Grosjean et al. | 72/56 |
| 5,697,948 A * | 12/1997 | Marin et al. | 606/198 |
| 5,749,880 A * | 5/1998 | Banas et al. | 606/198 |
| 5,776,141 A * | 7/1998 | Klein et al. | 623/1.11 |
| 5,876,448 A * | 3/1999 | Thompson et al. | 623/1.13 |
| 5,920,975 A * | 7/1999 | Morales | 29/282 |
| 5,928,258 A * | 7/1999 | Khan et al. | 606/191 |
| 6,063,092 A * | 5/2000 | Shin | 606/108 |
| 6,143,014 A * | 11/2000 | Dehdashtian et al. | 606/192 |
| 6,203,568 B1 | 3/2001 | Lombardi et al. | |
| 6,214,039 B1 * | 4/2001 | Banas et al. | 623/1.13 |
| 6,451,047 B2 * | 9/2002 | McCrea et al. | 623/1.13 |
| 6,471,718 B1 * | 10/2002 | Staehle et al. | 623/1.11 |
| 6,607,551 B1 * | 8/2003 | Sullivan et al. | 623/1.11 |
| 6,613,075 B1 * | 9/2003 | Healy et al. | 623/1.11 |
| 6,758,858 B2 * | 7/2004 | McCrea et al. | 623/1.13 |
| 6,776,791 B1 * | 8/2004 | Stallings et al. | 623/1.11 |
| 6,796,998 B2 * | 9/2004 | Schaldach et al. | 623/1.15 |
| 6,858,034 B1 * | 2/2005 | Hijlkema et al. | 606/108 |
| 6,945,989 B1 * | 9/2005 | Betelia et al. | 623/1.11 |
| 7,011,675 B2 * | 3/2006 | Hemerick et al. | 623/1.12 |
| 2001/0032009 A1 | 10/2001 | Layne et al. | |
| 2001/0039446 A1 * | 11/2001 | Edwin et al. | 623/1.13 |
| 2002/0029076 A1 * | 3/2002 | Yee | 623/1.13 |
| 2002/0038143 A1 * | 3/2002 | McCrea et al. | 623/1.13 |
| 2002/0058993 A1 * | 5/2002 | Landau et al. | 623/1.35 |
| 2002/0138966 A1 | 10/2002 | Motsenbocker | |
| 2002/0147490 A1 * | 10/2002 | Pletzer et al. | 623/1.11 |
| 2002/0156516 A1 | 10/2002 | Vardi et al. | |
| 2002/0193863 A1 * | 12/2002 | Rourke et al. | 623/1.11 |
| 2003/0032999 A1 * | 2/2003 | Huang | 623/1.11 |
| 2003/0153969 A1 | 8/2003 | Dehdashtian et al. | |
| 2004/0106977 A1 * | 6/2004 | Sullivan et al. | 623/1.12 |
| 2004/0204749 A1 * | 10/2004 | Gunderson | 623/1.12 |
| 2006/0184225 A1 * | 8/2006 | Pryor | 623/1.11 |
| 2006/0184226 A1 * | 8/2006 | Austin | 623/1.11 |
| 2006/0216404 A1 * | 9/2006 | Seyler et al. | 427/2.1 |
| 2007/0156251 A1 * | 7/2007 | Karmon | 623/23.61 |

FOREIGN PATENT DOCUMENTS

| | | |
|---|---|---|
| DE | 10212707 | 10/2003 |
| DE | 20306823 | 11/2003 |
| EP | 0596145 | 5/1994 |
| EP | 0788332 | 8/1997 |
| EP | 0836447 | 4/1998 |
| EP | 0873731 | 4/2000 |
| EP | 0826346 | 6/2003 |
| FR | 2742042 | 6/1997 |
| FR | 2760351 | 9/1998 |
| WO | WO 96/28115 | 9/1996 |
| WO | WO 98/31305 | 7/1998 |
| WO | WO 99/55255 | 11/1999 |
| WO | WO 01/05331 | 1/2001 |
| WO | WO 01/21103 | 3/2001 |
| WO | WO 01/34061 | 5/2001 |
| WO | WO 02/15820 | 2/2002 |
| WO | WO 03/003944 | 1/2003 |
| WO | WO 03/049641 | 6/2003 |
| WO | WO 2004/062458 | 7/2004 |
| WO | WO 2004/096091 | 11/2004 |

\* cited by examiner

LOADING AND DELIVERY OF SELF-EXPANDING STENTS

PRIORITY

This application is a national stage application under 35 USC §371 of International Application No. PCT/EP2004/004486, filed Apr. 28, 2004, claiming priority to United Kingdom Application No. GB 0309616.1, filed Apr. 28, 2003, each of which is incorporated by reference into this application as if fully set forth herein.

BACKGROUND OF THE INVENTION

This invention relates in one aspect to a method of loading a self-expanding stent into a delivery sheath, in which the stent in a radially confined delivery configuration is advanced axially into the sheath for delivery to a stenting site in which the sheath is withdrawn to release the stent for radial expansion. In another aspect, the invention relates to a self-expanding stent within a percutaneous transluminal delivery catheter that includes a sheath that withdraws proximally to release the stent at a stenting site, and a pusher within the sheath that retains the stent at the site during withdrawal of the sheath.

EP-A-788 332 discloses a self-expanding braided metallic stent tube and a delivery system that includes a soft annulus within the stent lumen that deforms and mechanically engages with the mesh of the stent for restraining the stent from axial movement relative to the inner catheter of the delivery system, during axial movement of a sleeve surrounding the stent. The disclosure of EP-A-596 145 is similar.

EP-A-836 447 discloses a system for delivering a self-expanding stent, in which a stopper ring on an inner catheter abuts the proximal end of the stent tube during proximal withdrawal of a sheath which surrounds the stent.

The number of materials that are biologically compatible, and available for making stents, are comparatively few. One preferred material is stainless steel. One can make stainless steel stents that are plastically deformed when they are expanded radially at the stenting site. One convenient way to expand such stents is by a balloon at the distal end of a balloon catheter. Otherwise, one can design a stainless steel stent to expand elastically when released at a stenting site. Typically, this is achieved by proximal withdrawal of a sheath on the distal end of the delivery catheter, that withdraws proximally to release the stent progressively, starting at its distal end.

Another suitable material is the nickel titanium shape memory alloy known under the trade mark NITINOL. Such stents are typically loaded into a delivery system at a low temperature when the crystal structure of the material is martensitic, and with a memory of a radially expanded shape, characteristic of a higher temperature austenitic crystalline structure. Remarkably, the nickel titanium material is biologically compatible and the martensite/austenite transformation occurs between room temperature and body temperature.

This invention is particularly applicable to self-expanding stents, irrespective of the mechanism of resilient radial expansion at the stenting site. However, the present Applicant has particular experience with nickel titanium shape memory alloy stents and the particular embodiments described below are based on such materials.

The tubular envelope of a stent usually has apertures through its wall thickness to permit radial expansion. Thus, an uncovered or "bare" stent has a tube wall that is normally liquid-permeable. However, there are many occasions when a stent with a liquid-impermeable wall that is not apertured would be desirable. To meet these needs, a family of "covered" stents have been developed. Applicant has particular experience with stent tubes provided with a covering of expanded polytetrafluoroethylene (ePTFE). Typically, the stent tube is covered by luminal and abluminal covering layers of ePTFE, which are bonded to each other through the apertures in the stent tube wall.

During manufacture of stents and delivery systems, attention must be paid to sterility. Specifically, one needs procedures for loading a covered stent into a catheter delivery system that will allow sterile conditions to be maintained, or at least thereafter achieved.

Typically, to introduce a covered self-expanding stent into a catheter delivery system, a tool needs to be provided that compresses the covered stent radially inwardly, down to a diameter which is smaller than the available diameter of the lumen of the delivery system that is to receive the compressed covered stent. Clearly, any structure within the lumen of the stent that resists further inward compression is better avoided, when the objective is to compress the stent radially inwardly as much as the system will tolerate, so as to keep the outside diameter of the delivery system at its distal tip as small as possible.

However, the stent has to be maintained at the stenting site during proximal withdrawal of the surrounding sheath, for progressive release of the stent at the stenting site. If there is no structure within the lumen of the stent, then the entire stress imposed on the stent, to prevent it moving proximally with the proximally withdrawing surrounding sheath, has to be carried on the proximal end annulus of the compressed stent. Often this is not really a problem, especially when the stent is short and not particularly highly compressed radially inwardly, and especially when friction between the compressed stent and the surrounding sheath can be brought to a particularly low value.

Nevertheless, it is important for management of fatigue resistance to avoid imposing on any point of the stent tube a level of stress that is higher than the designed maximum. A stent tube made of metal is susceptible to fatigue failure, if only because it is subject to cyclic stress at the frequency of the heartbeat of the body in which it is installed. For this reason, regulatory authorities require stringent fatigue performance standards which impose on manufacturers of stents and delivery systems an onerous burden to avoid any unforeseen stresses on the stent tube.

The state of the art contains numerous suggestions to use an element within the lumen of the stent to restrain the stent from proximal withdrawal when the surrounding sleeve is withdrawn proximally. However, these systems are of interest only for bare stents, because they rely upon mechanical interaction between surfaces on the stent pusher within the stent lumen, and boundary surfaces of apertures within the wall thickness of the stent tube.

BRIEF SUMMARY OF THE INVENTION

It is an object of the present invention to load self-expanding covered stents into catheter delivery systems which offers better management of stress within the stent tube, facilitates quality control and maintenance of sterile conditions, and is applicable to a range of stent tube designs.

According to one aspect of the present invention, there is provided a method of loading a self-expanding stent into a delivery sheath, as defined in claim 1 below.

According to a second aspect of the present invention there is provided a self-expanding stent within a percutaneous transluminal delivery catheter, as defined in claim 3 below.

By distributing over the full length of the stent tube lumen the forces which necessarily have to be imposed on the stent in order to:
1. load it into a delivery sheath; and/or
2. restrain it from proximal movement during proximal withdrawal of the delivery sheath during placement of the stent at the stenting site one can manage the distribution of stress within the stent tube so that it is distributed more or less homogeneously, rather than concentrated at one end of the stent tube. By using the covering of the stent as a link in the chain of stress distribution from the pusher to the sheath, one can further avoid any point at all within the metal stent tube which is subject to stress at a level higher than a prescribed design maximum. By their nature, stent coverings are more flexible than the stent tube itself, so have the capability to distribute stress from a point on a metallic stent pusher to an area, or volume, of the material of the stent tube.

Furthermore, the flexibility of the stent covering is sufficient to accommodate the protrusions of the pusher, irrespective where they lie in relation to the apertures of the stent lumen. With the present invention, there is no need to align in any way the protrusions of the stent pusher with the apertures of the stent lumen. Thus, a further technical effect of the present invention is valuable simplicity and speed of operation in loading a range of different covered stent products into their corresponding delivery systems.

Yet a further advantage of the present invention is that the stent pusher needs no undercut or rebated surfaces to achieve its effect, and the pusher has an outside diameter which is smaller than the inside or luminal diameter of the stent tube. These factors give greater reassurance that, when the stent has been placed, and the pusher has to be withdrawn from the stent lumen, there will be no inadvertent or unintended snagging of surfaces of the pusher on surfaces of the covered stent, or indeed of any bodily tissue that might impinge on the surfaces of the stent pusher after it has been withdrawn proximally out of the stent lumen.

Of particular interest in the present invention is a stent pusher with protrusions arranged helically. Such protrusions will achieve the desired pushing effect when the pusher is subject to axial stress. However, arranging the protrusions helically would allow the pusher to be withdrawn from the stent lumen, even while the stent is within the sheath of the delivery system, simply by "unscrewing" the shaft of the pusher until the helical protrusions emerge, by continued rotation of the pusher relative to the stent, out of the lumen of the stent. In this way, one can employ the stent pusher of the present invention as part of a system for loading a covered stent into a sheath, but then remove the pusher, and pass the sheath stent assembly onwards for incorporation into a delivery system which will use an entirely different stent pusher.

BRIEF DESCRIPTION OF THE DRAWINGS

For a better understanding of the present invention, and to show more clearly how the same may be carried into effect, reference will now be made to the accompanying drawings, in which.

DETAILED DESCRIPTION OF THE PREFERRED EMBODIMENTS

Figure 3:
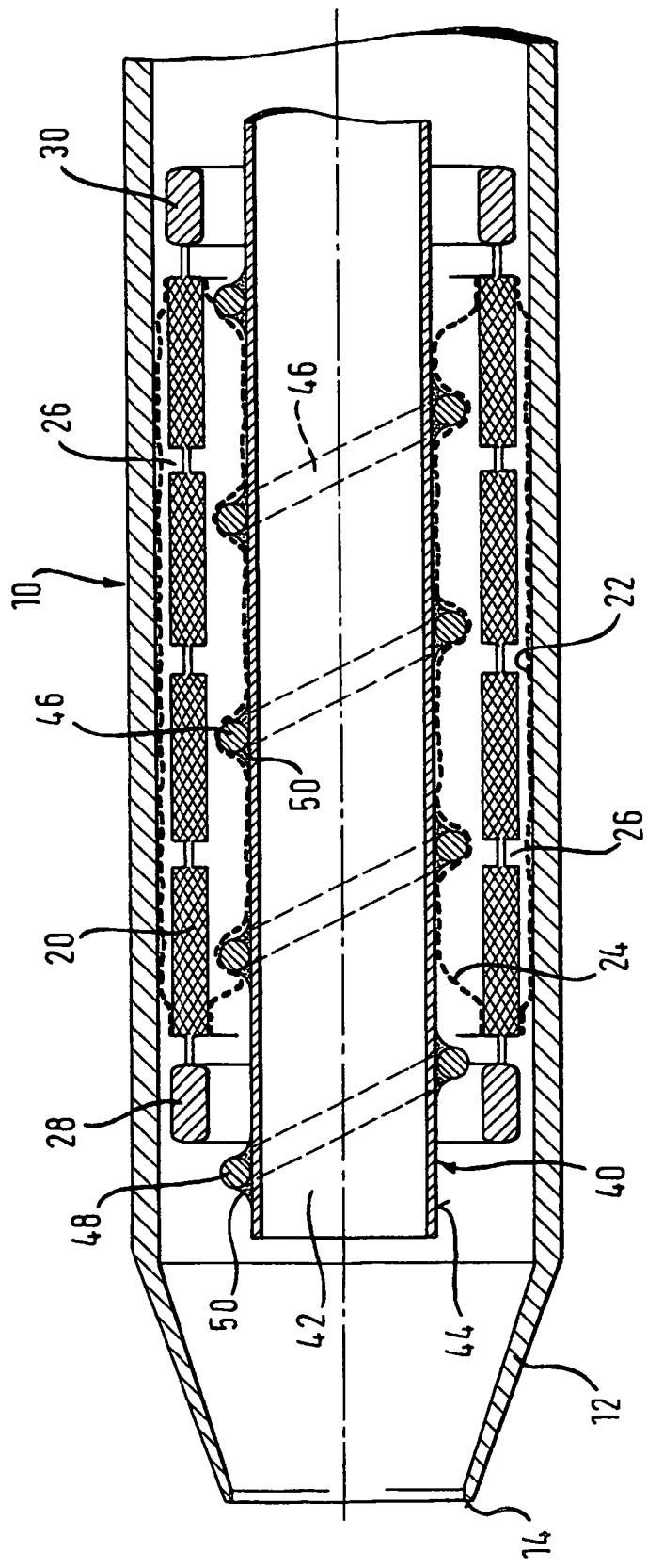
FIG. 3 is an axial diametral section through the distal tip of a stent delivery system which embodies the present invention.

FIG. 3 shows only the distal tip of the delivery system, but the remainder of the system is not part of the contribution which the present invention makes to the art and, in any event, is familiar to those skilled in this art. The basis components of a conventional delivery system for a self-expanding stent are an inner catheter and an outer sheath, the purpose of the outer sheath being to confine the self-expanding stent radially, to the small radius delivery configuration, until its release at the site of stenting. The purpose of the inner catheter is to restrain the stent from proximal movement with the sheath, while the sheath is being withdrawn proximally.

Looking at FIG. 3 of the drawings, the outer sheath 10 of the delivery system has an integral tapered tip 12 which narrows down to an end ring 14 of a diameter appropriate to receive a guidewire (not shown). Confined within the sheath is a covered stent of which the structural foundation is a stent body 20 which is an apertured tube of nickel titanium shape memory alloy. The stent is covered by an outer layer 22 of ePTFE on the abluminal surface of the stent body, and a covering layer 24 of ePTFE on the luminal inner surface of the stent body 20, with the inner and outer layers 24 and 22 being fused together where they can be pressed together within the apertures 26 of the stent body.

Between the luminal and abluminal surfaces of the stent body 20 is a wall thickness of the metallic stent material annulus. This annulus lies between the luminal and abluminal major surfaces of the stent body and, in the specification, we use the terminology "envelope" to indicate the generalised surfaces of the luminal and abluminal major wall surfaces of the stent body. Thus, the outer layer 22 lies outside the abluminal envelope stent body 20, except where it protrudes into the apertures 26 for fusing with the inner layer and, likewise, the inner layer 24 lies radially within the luminal envelope of the stent body 20 except where it protrudes radially outwardly into the stent body apertures 26.

The stent body carries a ring of tantalum radiopaque markers 28 at its distal end and a second ring of radiopaque tantalum markers 30 at its proximal end. It will be appreciated that the presence of these markers may further militate against pushing structures that bear against the end surface of the stent to be deployed.

The inner catheter 40 defines a guidewire lumen 42. Conveniently, the inner catheter 40 is based on a stainless steel hypo tube. This of course endows the entire delivery system with substantial pushability, but the hypo tube can also be made remarkably flexible for the desired trackability of the system through particularly tortuous bodily lumens. In any event, if stainless steel is not flexible enough for the distal zone of the delivery system, then it would be feasible to build the inner catheter 40 from other more flexible materials such as particular polymers.

The stent delivery system can be arranged as an over the wire system with a full length guidewire lumen, or a rapid exchange system with a guidewire lumen only in a distal zone of the system. The outer sheath 10 can be withdrawn by a full length outer catheter or a pull wire within a shaft lumen. For an example of delivery systems of the present Applicant, see WO 03/003944 and WO2004/062458.

The inner catheter has an abluminal surface 44 which carries on it a wire 46 arranged as a helix so as to provide a plurality of protrusions (at least when seen in section as in the drawing) on the abluminal surface 44. In the illustrated embodiment, the wire is of stainless steel, fixed to the stainless steel tube 40 by deposits 50 of a bonding material which could be a weld bead or a suitable adhesive.

In any event, as can be seen on the drawing, when the stent body is radially inwardly compressed down onto the inner catheter 40, the inner ePTFE layer 24 deforms to accommodate the protrusions 48, but the protrusions 48 do not reach radially outwardly as far as the luminal envelope of the stent body 20.

In use, when the illustrated distal tip zone has been brought to the site of stenting, the outer catheter 12 is carefully and progressively withdrawn proximally so that the tip stretches and slides over the outer ePTFE layer 22 of the stent, progressively releasing the stent, starting at its distal end near the markers 28.

As the stent progressively expands, the inner ePTFE layer 24 moves radially outwardly away from the protrusions 48 until, with complete withdrawal of the tip 12 proximally beyond the proximal ring of radiopaque markers 30, the stent is fully released. It will be appreciated that there is then a substantial annular gap between the lumen of the expanded stent and the envelope containing the protrusions 48, enabling the inner catheter 40 also to be withdrawn proximally from the lumen of the stent without any snagging of the inner catheter 40 on any part of the stent.

It will be appreciated that, for loading a stent into a sheath, an analogous sequence of steps may be performed, with radially inward compression of the stent body down onto the protrusions 48 of a loading tool which has a shape in section analogous to that of the inner catheter 40. Once the stent has been so compressed, a suitable sheath can be offered up to one end of the compressed stent tube, and then the stent can be urged axially into the sheath by imposing an axial force on the line of protrusions 48 through the tube 40 on which they amounted, so that this force is transferred from the protrusions 48 to the inner layer 24 and thence to the stent body 20 and the outer layer 22, so that the entire covered stent device is urged by the protrusions 48 into the receiving sheath.

A particular advantage of the helical structure of protrusions 48 as shown in the drawing is that the pusher within the stent lumen can be removed trouble-free from the lumen of the stent even when it is in a compressed configuration within a sheath as shown in the drawing, simply by "unscrewing" the pusher from within the stent lumen.

Figure 1:
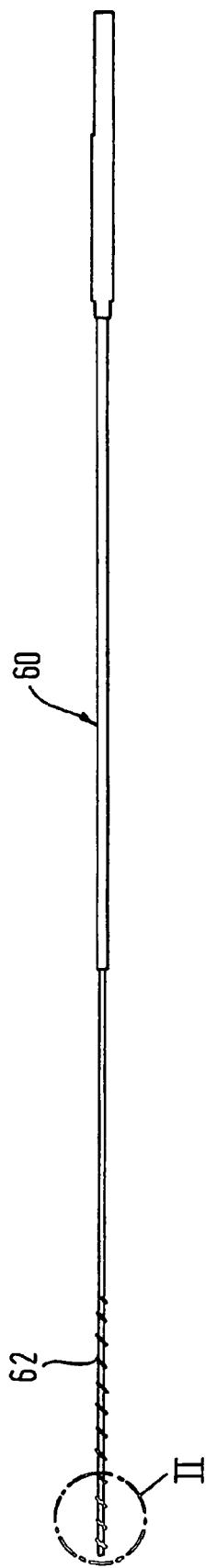
FIG. 1 is a side view of a tool for loading a covered self-expanding stent into a sheath.
Figure 2:
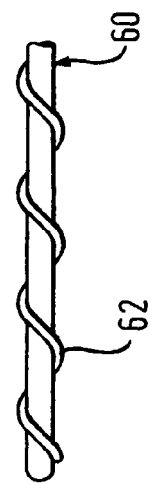
FIG. 2 is an enlarged view of the distal end (II) of the tool of FIG. 1.

Drawing FIGS. 1 and 2 show a suitable loading tool 60, long enough to push the covered stent along the full length of the outer catheter 10, after being compressed and introduced and advanced into the proximal end of the outer catheter. The tool 60 features at its distal end a radially-outwardly protruding wire spiral 62 with a configuration corresponding to that of the protrusions 48 and the inner catheter 40 (although non-corresponding configurations are also feasible). The covered stent is compressed around the protrusions 62 before the tool 60 is used to urge the covered stent by means of the protrusions 62, from the proximal to the distal end of the outer catheter.

The illustrated embodiment shows a system in which the tapered distal tip of the stent delivery system is carried on the distal end of the outer catheter. Those skilled in the art are well-aware that many proposed delivery systems feature a tapered tip on the inner catheter instead. The present invention is just as useful in such systems as it is in systems, as illustrated, with the tapered tip on the outer catheter.

The stent on which the present device operates can be an covered self-expanding stent. The stent which is the basis of the illustrated embodiment is the one that is the preferred embodiment of WO 2002/015820 which is cut from a nickel-titanium tube. However, the invention is equally applicable to other stent design philosophies, such as stents fabricated from wire (one example is the Gianturco "Z" stent made from zig zag wire rings) or other metals, such as stainless steel. The invention is particular useful for covered stents in which only the cover connects adjacent ones of a plurality of stenting rings, because the engagement of the pusher over the full length of the stent should avoid any tendency for the stent covering to "concertina" between the stenting rings when pushed only from its trailing (usually proximal) end.

Those skilled in the art will be able to recognise from this disclosure many other ways to realise the present invention besides that described with reference to the drawings.

What is claimed is:

1. A method of loading a self-expanding stent into a delivery sheath, comprising:
   i) providing said stent as a covered stent having a stent matrix with surfaces defining luminal and abluminal envelopes spaced apart by a stent wall thickness, a covering material bonded to the matrix lying radially inside the luminal envelope;
   ii) providing a stent pusher in a lumen defined by the stent, the stent pusher having protrusions distributed along the length of the stent lumen;
   iii) compressing the stent radially inwardly until the protrusions deform the covering material but do not reach radially outwardly as far as the luminal envelope; and
   iv) imposing an endwise force on the stent pusher so that the covering material transfers the pushing force from the protrusions of the stent pusher to the stent matrix to advance the stent into the sheath.

2. Method as claimed in claim 1, including the step of arranging the protrusions helically, so that the stent pusher can be withdrawn from the lumen of the stent, inside the sheath, by unscrewing the stent pusher relative to the stent lumen.

3. A delivery system including a self-expanding stent in a percutaneous transluminal delivery catheter that includes a sheath that withdraws proximally to release the stent at a stenting site, comprising:
   i) a pusher within the sheath that extends along the lumen of the stent and has radially outwardly extending protrusions distributed along the length of the stent lumen;
   ii) the stent being a covered stent having a matrix with surfaces defining luminal and abluminal envelopes spaced apart by a stent wall thickness, a covering material bonded to the matrix lying radially inside the luminal envelope; and
   iii) the stent being positioned over the protrusions such that the protrusions deform the covering material but do not reach radially outwardly as far as the luminal envelope.

4. The delivery system as claimed in claim 3, wherein the stent matrix comprises metal and the covering comprises expanded polytetrafluoroethylene.

5. The delivery system as claimed in claim 3, wherein the stent matrix is apertured and the covering is bonded to an abluminal stent covering layer through the apertures.

6. The delivery system as claimed in claim 3, wherein the stent matrix is formed from a nickel-titanium shape memory alloy.

7. The delivery system as claimed in claim 3, wherein said protrusions are the turns of a spiral.

8. The delivery system as claimed in claim 3, with a tapered distal tip on said sheath.

9. The delivery system as claimed in claim 3, with a tapered distal tip on said pusher, distal of said sheath.

10. A delivery system, comprising:
a self-expanding stent having a wall and a luminal and abluminal wall surface, a first covering layer positioned on at least the luminal wall surface;
an outer sheath having a distal end configured to receive and maintain the stent in a reduced diameter delivery configuration; and
an inner catheter having a distal end positioned within a lumen of the stent, the inner catheter including radially outwardly extending protrusions along the distal end that extend into the covering without intersecting a plane along the luminal wall surface.

11. The delivery system according to claim 10, further comprising a second covering layer on the abluminal surface of the stent, wherein the first covering layer is bonded to the second covering layer through apertures in the stent wall.

12. The delivery system according to claim 11, wherein the first and second covering layers are comprised of ePTFE.

13. The delivery system according to claim 10, further comprising a plurality of markers.

14. The delivery system according to claim 13, wherein the markers are arranged circumferentially about a proximal and distal end of the stent.

15. The delivery system according to claim 10, wherein the protrusions are formed by a wire arranged helically about the inner catheter.

16. The delivery system according to claim 15, wherein the inner catheter is comprised of stainless steel, and the wire is bonded to the inner catheter.

17. The delivery system according to claim 10, wherein the outer sheath includes a tapered distal end.

18. The delivery system according to claim 10, wherein the stent is cut from a nickel-titanium tube.

19. A method of loading a self-expanding stent into a delivery sheath, the stent including a covering layer on a luminal wall surface, comprising:
providing a stent pusher including protrusions on a distal end thereof;
radially compressing the stent over the protrusions such that the protrusions deform the covering layer but do not intersect a plane along the luminal wall surface; and
inserting the stent pusher and stent into the sheath.

20. The method according to claim 1, wherein the protrusions are arranged helically about the distal end of the stent pusher, further comprising the step of withdrawing the stent pusher by unscrewing it from the covering layer.

21. The delivery system according to claim 3, wherein the pusher has an outside diameter smaller than a luminal diameter of the stent.

22. The delivery system according to claim 8, wherein the tapered distal tip narrows to an end ring of a diameter appropriate to receive a guidewire.

23. The delivery system according to claim 10, wherein the inner catheter comprises a material selected from the group consisting of stainless steel, flexible polymer, and combinations thereof.

24. The delivery system according to claim 10, wherein the inner catheter defines a guidewire lumen.

25. The delivery system according to claim 10, wherein the delivery system comprises a rapid exchange system with the guidewire lumen only in a distal zone of the delivery system.

26. The delivery system according to claim 13, wherein the markers are comprised of tantalum.

27. The delivery system according to claim 15, wherein the wire is comprised of stainless steel.

* * * * *